United States Patent
Takeuchi et al.

(10) Patent No.: US 8,916,502 B2
(45) Date of Patent: *Dec. 23, 2014

(54) AGENT FOR IMPROVING LAWN GRASS QUALITIES

(75) Inventors: Yasutomo Takeuchi, Utsunomiya (JP); Shigeyuki Funada, Satte (JP)

(73) Assignee: Cosmo Oil Co., Ltd., Tokyo (JP)

( * ) Notice: Subject to any disclaimer, the term of this patent is extended or adjusted under 35 U.S.C. 154(b) by 296 days.

This patent is subject to a terminal disclaimer.

(21) Appl. No.: 12/866,113

(22) PCT Filed: Mar. 26, 2009

(86) PCT No.: PCT/JP2009/001350
§ 371 (c)(1),
(2), (4) Date: Aug. 4, 2010

(87) PCT Pub. No.: WO2009/139106
PCT Pub. Date: Nov. 19, 2009

(65) Prior Publication Data
US 2010/0317527 A1    Dec. 16, 2010

(30) Foreign Application Priority Data
May 13, 2008 (JP) .................. 2008-126018

(51) Int. Cl.
| | | |
|---|---|---|
| A01N 37/44 | (2006.01) | |
| A01N 37/00 | (2006.01) | |
| A01N 43/60 | (2006.01) | |
| A01N 43/54 | (2006.01) | |
| A01N 37/10 | (2006.01) | |
| A01N 43/00 | (2006.01) | |
| A01N 43/653 | (2006.01) | |
| A01N 43/40 | (2006.01) | |
| A01N 43/48 | (2006.01) | |
| A01N 47/10 | (2006.01) | |
| A01N 53/00 | (2006.01) | |
| A01N 43/64 | (2006.01) | |

(52) U.S. Cl.
CPC ..................... *A01N 37/44* (2013.01)
USPC ........... 504/147; 504/136; 504/139; 504/144; 504/174; 504/177; 504/181; 504/182; 504/239; 504/272; 504/313; 504/320; 514/561; 514/256; 514/383; 514/531; 514/557

(58) Field of Classification Search
CPC ....... A01N 37/44; A01N 37/42; A01N 43/40; A01N 43/54; A01N 43/653; A01N 2300/00
USPC ......... 504/136, 272, 320, 147, 139, 144, 174, 504/177, 181, 182, 239, 313; 514/666, 561, 514/256, 383, 531, 557
See application file for complete search history.

(56) References Cited

U.S. PATENT DOCUMENTS
| | | |
|---|---|---|
| 4,749,716 A | 6/1988 | Funaki et al. |
| 5,298,482 A | 3/1994 | Tanaka et al. |
| 2010/0234231 A1 | 9/2010 | Takeuchi et al. |
| 2010/0331183 A1 | 12/2010 | Takeuchi et al. |

FOREIGN PATENT DOCUMENTS
| | | |
|---|---|---|
| EP | 0 514 776 A1 | 11/1992 |
| EP | 0 714 600 A2 | 6/1996 |
| EP | 0 714 600 A3 | 6/1996 |
| EP | 2 130 435 A1 | 12/2009 |
| EP | 2 172 105 A1 | 4/2010 |
| JP | 56 25105 | 3/1981 |
| JP | 58 164501 | 9/1983 |
| JP | 1-163105 A | 6/1989 |
| JP | 4 338305 | 11/1992 |
| JP | 2007 217337 | 8/2007 |
| WO | WO 2005/080576 A1 | 9/2005 |
| WO | WO 2008/094567 A1 | 8/2008 |

OTHER PUBLICATIONS

Wilhelm Rademacher, "Growth Retardants: Effects on Gibberellin Biosynthesis and OtherMetabolic Pathways", Annual Reviews of Plant Physiology and Plant Molecular Biology, 2000, 51:501-531.*
U.S. Appl. No. 12/866,150, filed Aug. 4, 2010, Takeuchi, et al.
Otsuka, T. et al., "Creeping Bentgrass Oyobi Kentucky Bluegrass Ni Taisuru Prohexadion-Ca En No Taikansei Fuyo Koka", Journal of Japanese Society of Turfgrass Science, vol. 34, No. 1, pp. 15-17 and p. 88 (2005) ISSN: 0285-8800 (with English abstract).
Extended European Search Report issued Aug. 2, 2013, in Patent Application No. 09746313.7.

* cited by examiner

*Primary Examiner* — Abigail Fisher
*Assistant Examiner* — Nathan W Schlientz
(74) *Attorney, Agent, or Firm* — Oblon, Spivak, McClelland, Maier & Neustadt, L.L.P.

(57) ABSTRACT

An agent for improving lawn grass quality, which is excellent in promoting dwarfing of lawn grass, making the stem sturdy, increasing the leaf count, and improving greenness, is provided.

An agent for improving lawn grass quality containing, as active ingredients, 5-aminolevulinic acid represented by formula (1):

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group, or a derivative thereof or a salt of the acid or the derivative, and a gibberellin biosynthesis inhibitor.

9 Claims, No Drawings

AGENT FOR IMPROVING LAWN GRASS QUALITIES

FIELD OF THE INVENTION

The present invention relates to an agent for improving lawn grass quality, and more particularly, to an agent for improving lawn grass quality having one or more effects of promotion of dwarfing, by which elongation of lawn grass is suppressed; sturdiness of stem, by which the weight of the stem is increased; increase of leaf count, by which the leaf density is increased; and improvement of greenness, by which the extent of greenness is increased.

BACKGROUND OF THE INVENTION

Lawn grasses are widely used for the purpose of sports, leisure, ornamentation and protection, and they are particularly essential in golf fields. In regard to the management of lawn grass, although mowing poses physiological harm to the lawn grass, maintaining an appropriate grass height increases the density of stems and leaves, and suppresses germination of weeds. Therefore, it is very important to maintain the grass height by mowing. However, frequent mowing intended for maintaining the grass height requires efforts, and thus dwarfing agents for lawn grass have been used to reduce such efforts.

Known dwarfing agents for lawn grass include various gibberellin biosynthesis inhibitors, and cinnamic acid (Patent Document 1). However, these dwarfing agents for lawn grass do not still give sufficiently satisfactory results.

Furthermore, it is desirable for the lawn grass to have sturdy stems, a high density of leaves, and vivid green color, particularly for the purpose of sports, ornamentation and the like. 5-Aminolevulinic acid is known to make the stems of lawn grass sturdy, to increase the density of leaves, and to make the green color more vivid (Patent Document 2), but 5-aminolevulinic acid alone do not yield sufficiently satisfactory results.

Patent Document 1: JP-A-2007-217337
Patent Document 2: JP-A-04-338305

SUMMARY OF THE INVENTION

Problem to be Solved by the Invention

It is an object of the present invention to provide an agent for improving lawn grass quality, which improves the quality of lawn grass, particularly in the aspects of dwarfing of lawn grass, increase of stem weight, increase of leaf count, and sufficient improvement of greenness.

Means for Solving the Problem

The inventors of the present invention devotedly conducted an investigation under such circumstances, and they unexpectedly found that when a gibberellin biosynthesis inhibitor, which is a dwarfing agent, is used in combination with 5-aminolevulinic acid, a derivative thereof or a salt of the acid or the derivative, which has a growth promoting effect, not only the dwarfing effect is augmented as compared with the case of using a gibberellin biosynthesis inhibitor alone, but also the effects of making the stems sturdy, increasing the leaf count, and improving greenness can be synergistically increased, while the same effects are manifested weakly or in a reverse manner when the agents are used individually alone. Thus, the inventors completed the present invention.

That is, the present invention provides an agent for improving lawn grass quality containing, as active ingredients, 5-aminolevulinic acid represented by formula (1):

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group, or a derivative thereof, or a salt of the acid or the derivative, and a gibberellin biosynthesis inhibitor.

Furthermore, the improvement of lawn grass quality according to the present invention includes at least one of (a) promotion of dwarfing, (b) sturdiness of stems, (c) increase of leaf count, and (d) improvement of greenness.

The present invention also provides a method for improving lawn grass quality, including treating lawn grass with 5-aminolevulinic acid represented by the formula (I), a derivative thereof, or a salt of the acid or the derivative, and a gibberellin biosynthesis inhibitor.

Effect of the Invention

According to the present invention, the agent of the present invention can further promote dwarfing of lawn grass as compared with conventional dwarfing agents, and also can make the stems of lawn grass sturdier, further increase the leaf count, and further improve greenness, as compared with the case of using 5-aminolevulinic acid and a gibberellin biosynthesis inhibitor respectively alone. In regard to 5-aminolevulinic acid, since the compound is known to have a lawn grass growth promoting effect, the compound increases the grass height when used alone. However, when used in combination with a gibberellin biosynthesis inhibitor, 5-aminolevulinic acid gives an unexpected effect of decreasing the grass height, as compared with the case of using a gibberellin biosynthesis inhibitor alone. Furthermore, in regard to the gibberellin biosynthesis inhibitor, the agent hardly improves the stem, leaf count and greenness when used alone, since the agent inhibits biosynthesis of gibberellin, which is a plant hormone. However, when used in combination with 5-aminolevulinic acid, the gibberellin biosynthesis inhibitor gives unexpected effects of making the stems sturdy, increasing the leaf count, and improving greenness, as compared with the case of using 5-aminolevulinic acid alone.

DETAILED DESCRIPTION OF THE INVENTION

One of the active ingredients of the quality improving agent of the present invention includes 5-aminolevulinic acid, a derivative thereof (the formula (I)), or a salt of the acid or the derivative.

In the formula (1), the alkyl group represented by $R^1$ and $R^2$ is preferably a straight-chained or branched alkyl group having 1 to 24 carbon atoms, more preferably an alkyl group having 1 to 18 carbon atoms, and particularly preferably an alkyl group having 1 to 6 carbon atoms. Examples of the alkyl group having 1 to 6 carbon atoms include a methyl group, an ethyl group, an n-propyl group, an isopropyl group, an n-butyl group, and a sec-butyl group. The acyl group is preferably a straight-chained or branched alkanoyl group, alkenylcarbonyl group or aroyl group, each having 1 to 12 carbon atoms, and is particularly preferably an alkanoyl group having 1 to 6 carbon atoms. Examples of the acyl group include a formyl group, an acetyl group, a propionyl group, and a butyryl group. The alkoxycarbonyl group is preferably an alkoxycarbonyl group having 2 to 13 carbon atoms in total, and particularly preferably an alkoxycarbonyl group having 2 to 7 carbon atoms. Examples of the alkoxycarbonyl group include a methoxycarbonyl group, an ethoxycarbonyl group, an n-propoxycarbonyl group, and an isopropoxycarbonyl group. The aryl group is preferably an aryl group having 6 to 16 carbon atoms, and examples thereof include a phenyl group, and a naphthyl group. The aralkyl group is preferably a group formed from an aryl group having 6 to 16 carbon atoms and an alkyl group having 1 to 6 carbon atoms, and examples thereof include a benzyl group.

The alkoxy group represented by $R^3$ is preferably a straight-chained or branched alkoxy group having 1 to 24 carbon atoms, more preferably an alkoxy group having 1 to 16 carbon atoms, and particularly preferably an alkoxy group having 1 to 12 carbon atoms. Examples of the alkoxy group include a methoxy group, an ethoxy group, an n-propoxy group, an isopropoxy group, an n-butoxy group, a pentyloxy group, a hexyloxy group, an octyloxy group, a decyloxy group, and a dodecyloxy group. The acyloxy group is preferably a straight-chained or branched alkanoyloxy group having 1 to 12 carbon atoms, and particularly preferably an alkanoyloxy group having 1 to 6 carbon atoms. Examples of the acyloxy group include an acetoxy group, a propionyloxy group, and a butyryloxy group. The alkoxycarbonyloxy group is preferably an alkoxycarbonyloxy group having 2 to 13 carbon atoms in total, and particularly preferably an alkoxycarbonyloxy group having 2 to 7 carbon atoms in total. Examples of the alkoxycarbonyloxy group include a methoxycarbonyloxy group, an ethoxycarbonyloxy group, an n-propoxycarbonyloxy group, and an isopropoxycarbonyloxy group. The aryloxy group is preferably an aryloxy group having 6 to 16 carbon atoms, and examples thereof include a phenoxy group, and a naphthyloxy group. The aralkyloxy group is preferably a group having the aralkyl group mentioned above, and examples thereof include a benzyloxy group.

In the formula (1), $R^1$ and $R^2$ are each preferably a hydrogen atom. $R^3$ is preferably a hydroxyl group, an alkoxy group or an aralkyloxy group, more preferably a hydroxyl group or an alkoxy group having 1 to 12 carbon atoms, and particularly preferably a methoxy group or a hexyloxy group.

Examples of the 5-aminolevulinic acid derivatives include 5-aminolevulinic acid methyl ester, 5-aminolevulinic acid ethyl ester, 5-aminolevulinic acid propyl ester, 5-aminolevulinic acid butyl ester, 5-aminolevulinic acid pentyl ester, and 5-aminolevulinic acid hexyl ester. Particularly, 5-aminolevulinic acid methyl ester or 5-aminolevulinic acid hexyl ester is preferred.

Examples of the salts of 5-aminolevulinic acid and its derivatives include acid addition salts such as hydrochloride, phosphate, nitrate, sulfate, sulfonate, acetate, propionate, butyrate, valerate, citrate, fumarate, maleate and malate; and metal salts such as sodium salt, potassium salt and calcium salt. 5-aminolevulinic acid and salts thereof can be used singly, or as mixtures of two or more of these.

5-aminolevulinic acid, a derivative thereof, or a salt of the acid or the derivative can be produced according to any of chemical syntheses, and methods utilizing microorganisms or enzymes. For example, the methods described in JP-A-4-9360, JP-A-11-501914, JP-A-2005-314360, JP-A-2005-314361 and JP-A-2006-182753 may be mentioned. Products thereof can be used directly without going through separation and purification, as long as the products do not contain substances that are harmful to lawn grass. If the products contain any harmful substances, the products can be used after eliminating the harmful substances appropriately to a level that is not regarded as harmful.

Examples of the gibberellin biosynthesis inhibitor, which is one of the active ingredients of the agent for improving lawn grass quality of the present invention, include inabenfide (4'-chloro-2'-(α-hydroxybenzyl)isonicotinanilide), uniconazole P ((E)-(S)-1-(4-chlorophenyl)-4,4-dimethyl-2-(1H-1,2,4-triazol-1-yl)pent-1-en-3-ol), trinexapac-ethyl (ethyl=4-cyclopropyl-α-hydroxymethylene)-3,5-dioxocyclohexane carboxylate), paclobutrazol ((2RS,3RS)-1-(4-chlorophenyl)-4,4-dimethyl-2-(1H-1,2,4-triazol-1-yl)pentan-3-ol), prohexadione calcium salt (calcium 3-oxido-5-oxo-4-propionyl-3-cyclohexene carboxylate), flurprimidol (2-methylpyrimidin-5-yl-1-(4-trifluoromethoxyphenyl)propan-1-ol), ancymidol (α-cyclopropyl-α(4-methoxyphenyl)-5-pyrimidinemethanol), chlormequat (2-chloroethyltrimethylammonium=chloride), and daminozide (N-(dimethylamino)succinamide acid). Preferred examples include trinexapac-ethyl, paclobutrazol, prohexadione calcium salt and flurprimidol, and particularly preferred examples include paclobutrazol and prohexadione calcium salt.

The plants which are the targets of application of the quality improving agent of the present invention, are preferably lawn grasses, more preferably Colonial Bentgrass, Kentucky Bluegrass, Perennial Ryegrass, *Zoysia tenuifolia* and *Zoysia japonica*, and even more preferably *Zoysia tenuifolia* and bentgrass.

It will be acceptable if the agent for improving lawn grass quality of the present invention contains 5-aminolevulinic acid, a derivative thereof or a salt of the acid or the derivative, and a gibberellin biosynthesis inhibitor, but the agent can be further incorporated with, if necessary, plant growth regulators, sugars, amino acids, organic acids, alcohols, vitamins, minerals and the like, in addition to those ingredients.

Examples of the plant growth regulators used herein include brassinolides such as epibrassinolides; choline preparations such as choline chloride and choline nitrate; indolebutyric acid, indoleacetic acid, ethychlozate preparations, 1-naphthylacetamide preparations, isoprothiolane preparations, nicotinic acid amide preparations, hydroxyisoxazole preparations, calcium peroxide preparations, benzylaminopurine preparations, methasulfocarb preparations, oxyethylene docosanol preparations, ethephon preparations, cloxyfonac preparations, gibberellins, streptomycin preparations, daminozide preparations, benzylaminopurine preparations, 4-CPA preparations, ancymidol preparations, inabenfide preparations, chlormequat preparations, dikegulac preparations, mefluidide preparations, calcium carbonate preparations, and piperonyl butoxide preparations. The term " . . . preparations" as used herein means "drug formulations containing . . . ".

Examples of the sugars include glucose, sucrose, xylytol, sorbitol, galactose, xylose, mannose, arabinose, madulose, sucrose, ribose, rhamnose, fructose, maltose, lactose, and maltotriose.

Examples of the amino acids include asparagine, glutamine, histidine, tyrosine, glycine, arginine, alanine, tryptophan, methionine, valine, proline, leucine, lysine, and isoleucine.

Examples of the organic acids include formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, malic acid, caproic acid, caprylic acid, myristic acid, stearic acid, palmitic acid, pyruvic acid, a-ketoglutaric acid, and levulinic acid.

Examples of the alcohols include methanol, ethanol, propanol, butanol, pentanol, hexanol, and glycerol.

Examples of the vitamins include nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, α-tocopherol, β-tocopherol, γ-tocopherol, σ-tocopherol, p-hydroxybenzoic acid, biotin, folic acid, nicotinic acid, pantothenic acid, and α-liponic acid.

Examples of the minerals include nitrogen, phosphorus, potassium, calcium, boron, manganese, magnesium, zinc, copper, iron, molybdenum, and magnesium.

The agent for improving lawn grass quality of the present invention is put to use by administering to the roots or the stems and leaves of lawn grass, or to the soil and water in the surroundings. The agent may be in the form of a solid or may be in the form of an aqueous solution, at the time of administration. Specifically, the agent may be used for foliage treatment (foliage treatment agent) or may also be used for soil treatment (soil treatment agent).

The amount ratio of 5-aminolevulinic acid, a derivative thereof or a salt of the acid or the derivative to the gibberellin biosynthesis inhibitor, which are both active ingredients of the agent for improving lawn grass quality, is such that relative to 100 parts by weight of 5-aminolevulinic acid, a derivative thereof or a salt of the acid or the derivative, 2,000 to 30,000 parts by weight of the gibberellin biosynthesis inhibitor is preferred, and 3,000 to 15,000 parts by weight of the inhibitor is more preferred. It is preferable to appropriately determine the weight ratio in accordance with the type of the gibberellin biosynthesis inhibitor used.

The amount of administration of 5-aminolevulinic acid, a derivative thereof or a salt of the acid or the derivative, which is an active ingredient of the agent for improving lawn grass quality, is preferably 0.1 to 10,000 mg, particularly preferably 1 to 1,000 mg, and even more preferably 1 to 200 mg, per 10 ares.

The amount of the gibberellin biosynthesis inhibitor may vary depending on the type of the inhibitor, the amount is preferably 1 to 1,000 g, and more preferably 10 to 200 g, per 10 ares. Specifically, the amount of administration of trinexapac-ethyl is preferably 2 to 200 g, and more preferably 10 to 40 g, per 10 ares. The amount of administration of paclobutrazol is preferably 3.6 to 360 g, and more preferably 18 to 72 g, per 10 ares. The amount of administration of prohexadione calcium salt is preferably 2 g to 200 g, and more preferably 10 to 40 g, per 10 ares. The amount of administration of flurprimidol is preferably 8.4 to 840 g, and more preferably 42 to 168 g, per 10 ares . Furthermore, it is preferable to treat lawn grass with the agent prepared to have the drug content in the range described above, in an amount of 10 to 1000 L, and more preferably 20 to 300 L, per 10 ares.

In the case of using the agent as a foliage treatment agent, there is no particularly limitation on the type and the amount of use of a spreading agent that is used for plants for which it is difficult for a drug formulation to adhere to the leaf surface, such as monocotyledonous plants.

The agent for improving lawn grass quality of the present invention can be used as an agent for promoting dwarfing of lawn grass, an agent for making stems sturdy, an agent for increasing the leaf count, or an agent for improving greenness.

In regard to the timing for treating plants with the agent for improving lawn grass quality, the time for carrying out the treatment in particular is not limited, but it is preferable to carry out the treatment during the lawn grass does not wither.

It is preferable to simultaneously carry out the treatment with 5-aminolevulinic acid, a derivative thereof or a salt of the acid or the derivative, and the treatment with a gibberellin biosynthesis inhibitor, which components are the active ingredients of the subject agent, and it is more preferable to carry out the treatment with a mixture of the two components. However, the treatments may also be carried out at different times. In the case of carrying out the treatments at different times, it is preferable to first carry out a treatment with one component and then to carry out a treatment with the other one component within 10 days, and more preferably within 5 days.

EXAMPLES

Hereinafter, the present invention will be explained in more details by way of Examples, but the present invention is not intended to be limited to these.

Example 1

Effects of promoting dwarfing of lawn grass and making stems sturdy, exerted by 5-aminolevulinic acid hydrochloride and various gibberellin biosynthesis inhibitors A commercially available *Zoysia tenuifolia* sod was cut to a size of 10×10 cm. Uniform volcanic ash soil (andosol) was introduced into a vessel (1/44,444×10 a) in a sufficient amount per pot, and a chemical fertilizer (N—P—K=8-8-8) was applied thereon in an amount, in terms of nitrogen, of 2.6 kg-N/10 a. The cut *Zoysia tenuifolia* sod was transplanted into the pot. After survival of the lawn grass was confirmed, a foliage treatment was carried out using combinations of various gibberellin biosynthesis inhibitors and 5-aminolevulinic acid hydrochloride (amount of treatment 600 mg/10 a), in an amount of treating liquid of 150 L/10 a. The grass height was measured 26 days after the treatment, and thereby the dwarfing effect was investigated. Furthermore, in order to show that the combination of 5-aminolevulinic acid hydrochloride and a gibberellin biosynthesis inhibitor promotes the growth of lawn grass stems, the grass stems were harvested 4 months after the treatment, and the dry weight was measured.

The results of the grass height and the stem dry weight are presented in Tables 1 to 4.

TABLE 1

Effect of promoting dwarfing exerted by 5-aminolevulinic acid hydrochloride and prohexadione calcium salt

| Amount of treatment of 5-aminolevulinic acid hydrochloride (mg/10 a) | Gibberellin biosynthesis inhibitor and amount of treatment (g/10 a) | Grass height (cm) | Dry weight of shoots (g) | Dry weight of stems (g) |
|---|---|---|---|---|
| 0 | 0 | 4.0 | 0.46 | 12.4 |
| 600 | 0 | 4.2 | 0.90 | 12.0 |
| 0 | Prohexadione calcium salt 20 | 3.5 | 0.72 | 11.3 |
| 600 | Prohexadione calcium salt 20 | 2.8 | 0.52 | 13.5 |

As shown in Table 1, when 5-aminolevulinic acid hydrochloride and prohexadione calcium salt were used in combination to carry out a treatment, although the two compounds respectively show different responses with regard to lawn grass when used individually, such as an increase in the grass height and a decrease in the grass height, a decrease in the grass height was observed to an extent that is more than what is obtained by a treatment with the prohexadione calcium salt alone. Thus, it was obvious that dwarfing was promoted. Furthermore, it was confirmed from the results of the dry weight of stems of lawn grass, that the growth of stems was promoted by the treatment with 5-aminolevulinic acid hydrochloride and prohexadione calcium salt, and the stems became sturdy. From these results, it was found that the product of the present invention has effects of promoting dwarfing and making stems sturdy.

TABLE 2

Effect of promoting dwarfing exerted by 5-aminolevulinic acid hydrochloride and trinexapac-ethyl

| Amount of treatment of 5-aminolevulinic acid hydrochloride (mg/10 a) | Gibberellin biosynthesis inhibitor and amount of treatment (g/10 a) | Grass height (cm) | Dry weight of shoots (g) | Dry weight of stems (g) |
|---|---|---|---|---|
| 0 | 0 | 4.0 | 0.46 | 12.4 |
| 600 | 0 | 4.2 | 0.90 | 12.0 |
| 0 | Trinexapac-ethyl 20 | 3.5 | 0.44 | 12.8 |
| 600 | Trinexapac-ethyl 20 | 2.5 | 0.36 | 15.2 |

As shown in Table 2, when 5-aminolevulinic acid hydrochloride and trinexapac-ethyl were used in combination to carry out a treatment, although the two compounds respectively show different responses to lawn grass when used individually, such as an increase in the grass height and a decrease in the grass height, a decrease in the grass height was observed to an extent that is more than what is obtained by a treatment with trinexapac-ethyl alone. Thus, it was obvious that dwarfing was promoted. Furthermore, it was confirmed from the results of the dry weight of stems of lawn grass, that the growth of stems was promoted by the treatment with 5-aminolevulinic acid hydrochloride and trinexapac-ethyl, and the stems became sturdy. From these results, it was found that the product of the present invention has effects of promoting dwarfing and making stems sturdy.

TABLE 3

Effect of promoting dwarfing exerted by 5-aminolevulinic acid hydrochloride and paclobutrazol

| Amount of treatment of 5-aminolevulinic acid hydrochloride (mg/10 a) | Gibberellin biosynthesis inhibitor and amount of treatment (g/10 a) | Grass height (cm) | Dry weight of shoots (g) | Dry weight of stems (g) |
|---|---|---|---|---|
| 0 | 0 | 4.0 | 0.46 | 12.4 |
| 600 | 0 | 4.2 | 0.90 | 12.0 |
| 0 | paclobutrazol 36 | 3.5 | 0.81 | 14.8 |
| 600 | paclobutrazol 36 | 2.6 | 0.61 | 20.9 |

As shown in Table 3, when 5-aminolevulinic acid hydrochloride and paclobutrazol were used in combination to carry out a treatment, although the two compounds respectively show different responses to lawn grass when used individually, such as an increase in the grass height and a decrease in the grass height, a decrease in the grass height was observed to an extent that is more than what is obtained by a treatment with paclobutrazol alone. Thus, it was obvious that dwarfing was promoted. Furthermore, it was confirmed from the results of the dry weight of stems of lawn grass, that the growth of stems was promoted by the treatment with 5-aminolevulinic acid hydrochloride and paclobutrazole, and the stems became sturdy. From these results, it was found that the product of the present invention has effects of promoting dwarfing and making stems sturdy.

TABLE 4

Effect of promoting dwarfing exerted by 5-aminolevulinic acid hydrochloride and flurprimidol

| Amount of treatment of 5-aminolevulinic acid hydrochloride (mg/10 a) | Gibberellin biosynthesis inhibitor and amount of treatment (g/10 a) | Grass height (cm) | Dry weight of shoots (g) | Dry weight of stems (g) |
|---|---|---|---|---|
| 0 | 0 | 4.0 | 0.46 | 12.4 |
| 600 | 0 | 4.2 | 0.90 | 12.0 |
| 0 | Flurprimidol 84 | 3.1 | 0.64 | 13.6 |
| 600 | Flurprimidol 84 | 2.8 | 0.67 | 15.8 |

As shown in Table 4, when 5-aminolevulinic acid hydrochloride and flurprimidol were used in combination to carry out a treatment, although the two compounds respectively show different responses to lawn grass when used individually, such as an increase in the grass height and a decrease in the grass height, a decrease in the grass height was observed to an extent that is more than what is obtained by a treatment with flurprimidol alone. Thus, it was obvious that dwarfing was promoted. Furthermore, it was confirmed from the results of the dry weight of stems of lawn grass, that the growth of stems was promoted by the treatment with 5-aminolevulinic acid hydrochloride and flurprimidol, and the stems became sturdy. From these results, it was found that the product of the present invention has effects of promoting dwarfing and making stems sturdy.

Example 2

Effects of increasing leaf count and improving greenness, exerted by 5-aminolevulinic acid hydrochloride and gibberellin biosynthesis inhibitor A commercially available bentgrass sod was cut into a circular form having a diameter of 10 cm. Uniform volcanic ash soil (andosol) was introduced into a vessel (1/17,500×10 a) in a sufficient amount per pot, and a liquid fertilizer (Hyponica) was applied thereon in an amount, in terms of nitrogen, of 3 kg-N/10 a. The cut bentgrass sod was transplanted into the pot. After survival of the lawn grass was confirmed, a foliage treatment was carried out using combinations of gibberellin biosynthesis inhibitors and 5-aminolevulinic acid hydrochloride (amount of treatment 200 mg/10 a), in an amount of treating liquid of 150 L/10 a. The number of lawn grass leaves was measured 30 days after the treatment, using a magnifying glass, and the L*a*b* values of lawn grass were measured using a colorimeter (manufactured by Konica Minolta Sensing, Inc.).

The measurement results for the leaf count and L*a*b* values are presented in Table 5.

TABLE 5

| Amount of treatment of 5-amino-levulinic acid hydrochloride (mg/10 a) | Gibberellin biosynthesis inhibitor and amount of treatment (g/10 a) | Plant count of lawn grass (plants/9 cm²) | Color system (L*/a*/b*) |
|---|---|---|---|
| 0 | 0 | 47.5 | 33.9/−8.6/18.1 |
| 200 | 0 | 54.2 | 34.0/−8.8/17.6 |
| 0 | Prohexadione calcium salt 12.5 | 65.5 | 33.2/−8.9/17.0 |
| 200 | Prohexadione calcium salt 12.5 | 78.8 | 33.2/−9.7/17.3 |

As shown in Table 5, although 5-aminolevulinic acid hydrochloride and a gibberellin biosynthesis inhibitor increase the leaf count of lawn grass when used individually on lawn grass, it was confirmed that when the two compounds are used in combination to carry out a treatment, the leaf count increases to an extent that is more than the summation of individual effects. Furthermore, it was also confirmed that when 5-aminolevulinic acid salt and a gibberellin biosynthesis inhibitor are used in combination, the a* value becomes more negative (the color becomes greener). From these results, it was found that the product of the present invention has effects of increasing the leaf count of lawn grass and improving greenness.

The invention claimed is:

1. A method for improving *Zoysia* or bentgrass lawn grass quality, comprising: treating lawn grass comprising *Zoysia* or bentgrass with a composition comprising:
   (i) 5-aminolevulinic acid or a salt thereof, and
   (ii) at least one gibberellin biosynthesis inhibitor selected from the group consisting of trinexapac-ethyl, paclobutrazol, prohexadione calcium salt, and flurprimidol;
   wherein said composition contains 2,000 to 30,000 parts by weight of the at least one gibberellin biosynthesis inhibitor based on 100 parts by weight of the 5-aminolevulinic acid or salt thereof.

2. The method for improving lawn grass quality according to claim 1, wherein (i) and (ii) are mixed prior to treating the lawn grass.

3. The method for improving lawn grass quality according to claim 1, wherein said lawn grass comprises *Zoysia tenuifolia*.

4. The method for improving lawn grass quality according to claim 1, wherein said lawn grass comprises bentgrass.

5. The method of claim 1, wherein (ii) is trinexapac-ethyl.

6. The method of claim 1, wherein (ii) is paclobutrazol.

7. The method of claim 1, wherein (ii) is prohexadione calcium salt.

8. The method of claim 1, wherein (ii) is flurprimidol.

9. The method of claim 1, wherein said composition produces at least one of (a) promotion of dwarfing or (b) sturdiness of stems when contacted with *Zoysia tenuifolia* when compared to *Zoysia tenuifolia* contacted only with (i) or (ii); or produces (c) an increase of leaf count or (d) improvement of greenness when contacted with bentgrass when compared to bentgrass contacted only with (i) or (ii).

* * * * *